US010537419B2

(12) United States Patent
Kratzberg et al.

(10) Patent No.: US 10,537,419 B2
(45) Date of Patent: Jan. 21, 2020

(54) PROSTHESIS WITH BRANCHED PORTION

(71) Applicant: Cook Medical Technologies LLC, Bloomington, IN (US)

(72) Inventors: Jarin A. Kratzberg, Lafayette, IN (US); Blayne A. Roeder, Bloomington, IN (US); Jennifer Stacy, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 15/794,550

(22) Filed: Oct. 26, 2017

(65) Prior Publication Data

US 2018/0116783 A1    May 3, 2018

Related U.S. Application Data

(60) Provisional application No. 62/413,574, filed on Oct. 27, 2016.

(51) Int. Cl.
| | | |
|---|---|---|
| *A61F 2/82* | (2013.01) | |
| *A61F 2/07* | (2013.01) | |
| *A61F 2/06* | (2013.01) | |
| *A61F 2/966* | (2013.01) | |
| *A61F 2/958* | (2013.01) | |

(52) U.S. Cl.
CPC .................. *A61F 2/07* (2013.01); *A61F 2/82* (2013.01); *A61F 2/958* (2013.01); *A61F 2/966* (2013.01); *A61F 2002/061* (2013.01); *A61F 2002/067* (2013.01); *A61F 2002/075* (2013.01); *A61F 2002/826* (2013.01); *A61F 2220/0075* (2013.01); *A61F 2240/001* (2013.01); *A61F 2240/002* (2013.01); *A61F 2250/0098* (2013.01)

(58) Field of Classification Search
CPC ...... A61F 2/07; A61F 2/82; A61F 2/89; A61F 2/06; A61F 2002/065; A61F 2/856
See application file for complete search history.

(56) References Cited

U.S. PATENT DOCUMENTS

| | | |
|---|---|---|
| 6,206,931 B1 | 3/2001 | Cook et al. |
| 7,407,509 B2 | 8/2008 | Greenberg et al. |
| (Continued) | | |

FOREIGN PATENT DOCUMENTS

WO    WO 2008/021557 A1    2/2008

OTHER PUBLICATIONS

Extended European Search Report for EP Application No. 17275174.5 dated Apr. 20, 2018, 8 pages.

*Primary Examiner* — Alvin J Stewart
(74) *Attorney, Agent, or Firm* — Brinks Gilson & Lione

(57) ABSTRACT

Examples of prostheses are provided having an internal branch. A tubular graft body of the prosthesis defines a main lumen extending between an inflow end and an outflow end of the graft body. A stent structure is coupled along the graft body. A trough is at least partially defined by a trough wall extending into the main lumen from a sidewall of the graft body. A side branch defines a branch lumen and extends from the trough within the main lumen towards one of the inflow or outflow ends of the graft body. A branch lumen facing surface of the trough wall is a continuous surface with an outer surface of the sidewall of the graft body. A boundary of the trough may be configured to provide a smooth transition surface between the trough and the sidewall.

15 Claims, 8 Drawing Sheets

(56) References Cited

U.S. PATENT DOCUMENTS

| | | | |
|---|---|---|---|
| 7,488,344 B2 | 2/2009 | Hartley et al. | |
| 7,537,606 B2 | 5/2009 | Hartley et al. | |
| 7,611,529 B2 | 11/2009 | Greenberg et al. | |
| 7,645,298 B2 * | 1/2010 | Hartley | A61F 2/07 623/1.13 |
| 7,828,837 B2 * | 11/2010 | Khoury | A61F 2/07 623/1.16 |
| 8,771,336 B2 * | 7/2014 | Roeder | A61F 2/07 623/1.13 |
| 8,808,358 B2 * | 8/2014 | Khoury | A61F 2/07 623/1.35 |
| 9,101,456 B2 * | 8/2015 | Hartley | A61F 2/07 |
| 9,149,382 B2 * | 10/2015 | Greenberg | A61F 2/07 |
| 9,649,188 B2 * | 5/2017 | Hartley | A61F 2/07 |
| 9,655,711 B2 * | 5/2017 | Hartley | A61F 2/07 |
| 9,918,823 B2 * | 3/2018 | Hartley | A61F 2/07 |
| 2006/0095118 A1 | 5/2006 | Hartley | |
| 2009/0171451 A1 | 7/2009 | Kuppurathanam et al. | |
| 2009/0204198 A1 | 8/2009 | Jensen et al. | |
| 2010/0249899 A1 * | 9/2010 | Chuter | A61F 2/07 623/1.13 |
| 2011/0257731 A1 * | 10/2011 | Hartley | A61F 2/07 623/1.35 |
| 2011/0313512 A1 * | 12/2011 | Hartley | A61F 2/07 623/1.35 |
| 2012/0130478 A1 | 5/2012 | Shaw | |
| 2012/0271401 A1 | 10/2012 | Bruszewski et al. | |
| 2012/0296414 A1 * | 11/2012 | Hartley | A61F 2/07 623/1.13 |
| 2013/0079870 A1 * | 3/2013 | Roeder | A61F 2/07 623/1.35 |
| 2013/0138199 A1 | 5/2013 | Ivancev et al. | |
| 2013/0184806 A1 | 7/2013 | Arbefeuille et al. | |
| 2014/0094902 A1 * | 4/2014 | Khoury | A61F 2/07 623/1.35 |
| 2014/0180393 A1 * | 6/2014 | Roeder | A61F 2/07 623/1.15 |
| 2014/0277347 A1 * | 9/2014 | Daugherty | A61F 2/856 623/1.11 |
| 2015/0012080 A1 | 1/2015 | Barrand | |
| 2016/0106564 A1 | 4/2016 | Roeder et al. | |
| 2016/0193032 A1 | 7/2016 | Dake et al. | |
| 2017/0128189 A1 * | 5/2017 | Wang | A61F 2/06 |
| 2017/0181838 A1 * | 6/2017 | Eller | A61F 2/92 |
| 2018/0036110 A1 * | 2/2018 | King | A61F 2/07 |

* cited by examiner

PROSTHESIS WITH BRANCHED PORTION

RELATED APPLICATIONS

The application claims the benefit of Provisional U.S. patent application Ser. No. 62/413,574, filed Oct. 27, 2016, which is hereby incorporated by reference.

BACKGROUND

The present disclosure relates generally to medical devices for implantation within a human or animal body for repair of damaged vessels, ducts, or other physiological pathways, and particularly, to prostheses with side branch lumens.

Endovascular methods have been proposed for treatment of diseases of the aorta such as aortic dissection and aortic aneurysm. Using prostheses, such as stent grafts, to treat aneurysms is common in the medical field. Stent grafts are deployed by accessing a vasculature with a small incision in the skin and guiding a delivery system to the target area. This endoluminal delivery is less invasive and generally preferred over more intrusive forms of surgery. Multiple stent grafts may be implanted using endoluminal delivery to provide a system of interconnected stent grafts. Interconnected stent grafts can be made of fenestrated stent grafts and smaller side branch grafts, including bifurcated components.

Such methods have been proposed particularly when the diseased portion of the aorta is adjacent the aorta bifurcation. But when the diseased portion of the aorta is located higher up in the aorta, for example, in the region of the descending aorta adjacent the thoracic arch or in the ascending aorta, endovascular techniques for treating these diseases are somewhat more difficult because of the arched or curved nature of the thoracic arch, the presence of major arteries in the region, and the proximity to the heart.

For instance, for treatment of thoracic aortic aneurysms and/or dissections in particular, it is necessary to introduce the stent graft high up in the aorta and in a region of the aorta which is curved and where there can be strong blood flow. Furthermore, in the thoracic aorta there are major branch vessels extending therefrom, such as the brachiocephalic, carotid and/or subclavian arteries. During and/or after treatment of an aneurysm or dissection in the region of the thoracic arch, it is desirable for blood supply to continue to flow to these branch arteries. For this purpose, fenestrations or side branches are provided in a stent graft that is placed in that region, through which side arms or branch extensions may be deployed and extend into the brachiocephalic, carotid and/or subclavian arteries, for example.

Custom made devices, including scalloped and fenestrated devices, have been used in situations where the arch vessels are compromised and entire coverage of the aortic arch is not required. However, deployment of these devices may be difficult.

SUMMARY

In one example, a prosthesis is provided. The prosthesis includes a tubular graft body, a stent structure, a trough and a tubular side branch. The tubular graft body includes a sidewall extending between an inflow end and an outflow end, defining a main lumen between the outflow and inflow ends. The stent structure is coupled along the graft body. The trough is at least partially defined by a trough wall extending from the sidewall. The tubular side branch defines a branch lumen and extends from the trough towards one of the inflow or outflow ends of the graft body. The trough, the branch lumen, and the main lumen are in fluid communication. The trough wall includes a branch lumen facing surface disposed to face the branch lumen. The branch lumen facing surface includes an unobstructed path to outside to the sidewall.

In another example, a prosthesis includes a tubular graft body defining a main lumen extending between an inflow end and an outflow end of the graft body. A stent structure is coupled along the graft body. A trough is defined by a boundary formed at a sidewall of the graft body. A portion of the boundary provides an unobstructed transition surface between the trough and the sidewall. An internal branch defines a branch lumen and extends from the trough towards one of the inflow or outflow ends of the graft body within the main lumen. The trough, the branch lumen, and the main lumen are in fluid communication.

In another example, a method of forming a prosthesis is provided including one or more of the following steps. A step includes forming a tab cutout in a sidewall of a tubular graft body, the graft body defining a main lumen extending between an inflow end and an outflow end of the graft body. A step includes coupling a first end opening of a tubular graft branch to the tab cutout, wherein the tab cutout is disposed away from the main lumen. A step includes coupling a trough graft wall between the tab cutout and the sidewall to define a trough disposed between the sidewall and the graft branch.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

Figure 1:
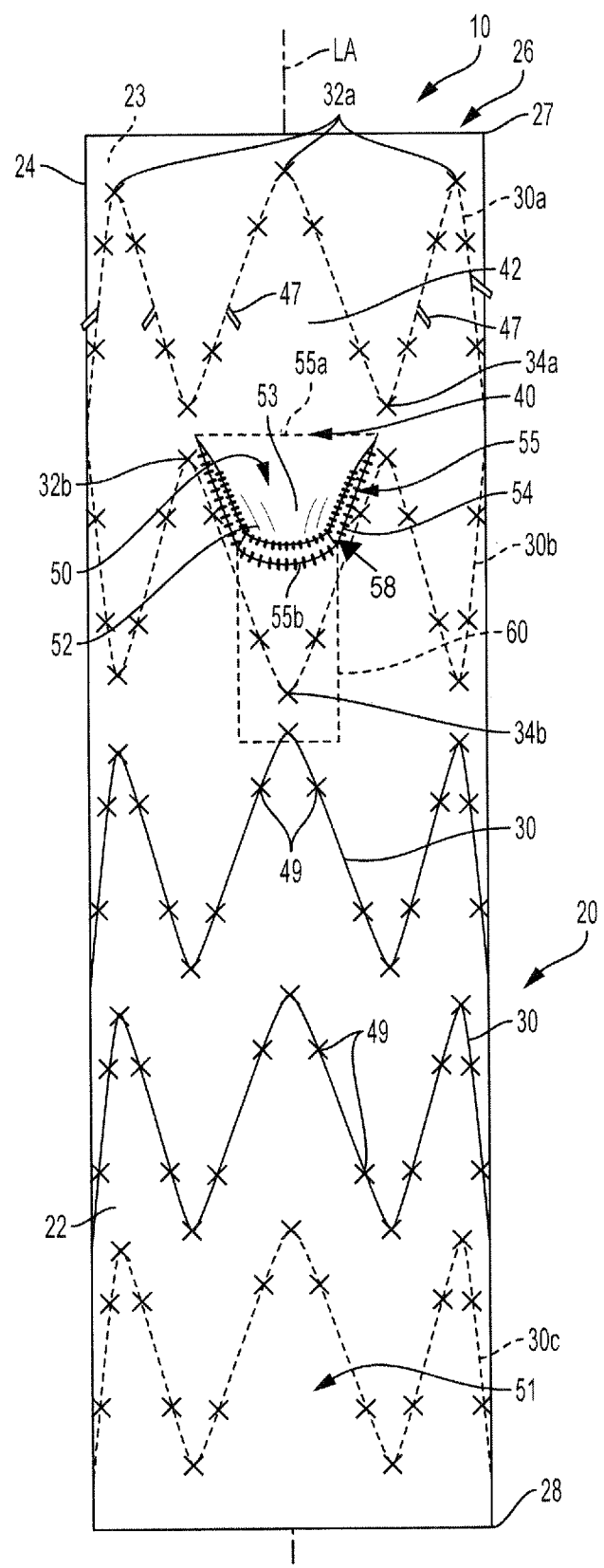
FIG. 1 is a side view of a prosthesis having one example of a trough portion in communication with a side branch.
Figure 2:
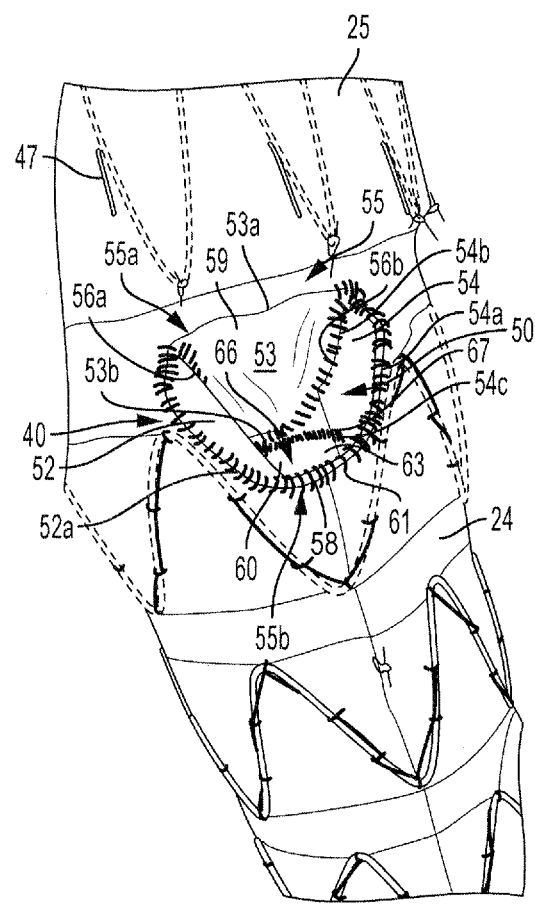
FIG. 2 is a perspective partial view of the trough portion and the side branch of the prosthesis depicted in FIG. 1.

Prostheses 10, 210 are disclosed for implantation within a human or animal body for repair of damaged primary vessels, ducts, or other physiological pathways with branch vessels, ducts, or pathways. In a particular example, the prosthesis may be implanted for suitable treatment of diseases of the aorta such as aortic dissection and aortic aneurysm, and in particular, the aortic arch or descending aorta distal to the subclavian artery. The main body of the prosthesis may be implanted into a primary vessel, and the branch opening may be used to provide access and/or blood perfusion via an internal or external side branch to a branch vessel, such as, for example, the subclavian artery, extending from the primary vessel. The lumen of the side branch may be used as a conduit to implant a connector prosthesis between the side branch and the branch vessel. The side branches of the prostheses described herein may be configured to reduce snagging or otherwise remove impediments to devices (wires, catheters, sheaths, etc.) passing between the main lumen of the prosthesis and the branch lumen of the side branch. For example, the branches may include a trough coupled from the sidewall. The trough may include an unobstructed path for such devices, for example, a path that is stitchless and/or frameless. The side branch configurations may minimize the time and mental fatigue required to achieve cannulation of such branch vessels. The prostheses described herein with the position and shape of the fenestration relative to the prosthesis end may improve sealing of the prosthesis along the primary vessel at the intersection of the branch vessel, such as, for example, the aorta arch, where separation between adjacent branch vessels, such as, for example, the subclavian and carotid arteries, is minimal.

In the present application, the term "proximal" when referring to a delivery device refers to a direction that is farthest away from an operator using a delivery device, while the term "distal" refers to a direction that is generally closest to the operator using the delivery device. The proximal and distal ends of a delivery device may also be referred to as an introduction end of the delivery device and an operator end of the delivery device, respectively. The term "operator end" of the delivery device is that portion of the device that is intended to remain outside of a patient during a procedure. The term "introduction end" of the delivery device, which is opposite to the operator end, is that portion of the device that is intended to be inserted within a patient during a procedure. When referring to the prosthesis itself relative to the delivery device, the proximal end of the prosthesis is that part of the prosthesis closest in proximity to the introduction end of the delivery device and the distal end of the prosthesis is that end that is closest in proximity to the operator end of the delivery device. When referring to the prosthesis relative to placement in the human body of the patient, the ends of the various devices and parts of devices may be referred to as the inflow end (that end that receives fluid first, and the outflow end (that end from which the fluid exits).

FIG. 1 depicts one example of a prosthesis 10. The prosthesis 10 may include a graft body 20. The graft body 20 may include a graft material 22 having an inner surface 23 and an outer surface 24 separated from one another to define a wall thickness of the graft body sidewall 25. The graft body 20 may be shaped and sized to correspond to the vessel to which the graft body is to be implanted. For example, the graft body 20 may be shaped as a generally tubular member having a substantially cylindrical shape, although some axial regions of the graft body 20 may be tapered. The inner surface 23 of the graft material 22 may define a main lumen 26 extending longitudinally within the graft body 20 between a proximal, inflow end 27 and a distal, outflow end 28 thereof along a longitudinal axis LA. The main lumen 26 may be suitable for passing a fluid such as, for example, blood therethrough.

The term "graft" describes an object, device, or structure that is joined or that is capable of being joined to a body part to enhance, repair, or replace a portion or a function of that body part. Grafts that can be used to repair body vessels include, for example, films, coatings, or sheets of material that are formed or adapted to conform to the body vessel that is being enhanced, repaired, or replaced. The graft material 22 may be formed from a biocompatible material that is substantially non-toxic in the in vivo environment of its intended use and substantially unrejected by the patient's physiological system (i.e., is non-antigenic). For example, the graft material 22 may be made of an expanded polytetrafluoroethylene (ePTFE), polytetrafluoroethylene (PTFE), silicone, polyurethane, polyamide (nylon), polyethylene, polypropylene, polyaramids, polyacrylonitrile, cellulose, or another flexible biocompatible material. The graft material 22 also may be made of known fabric graft materials, for example, woven polyester such as DACRON® from Invista (Wichita, Kans.), polyetherurethanes such as THORALON® from Thoratec Corporation (Pleasanton, Calif.), or polyethylene such as an ultra-high molecular weight polyethylene (UHMwPE) such as DYNEEMA® from DSM Dyneema LLC (Stanley, N.C.). Additionally, or alternatively, materials that are not inherently biocompatible may be subjected to surface modifications to render the materials biocompatible. Examples of surface modifications may include, for example, graft polymerization of biocompatible polymers on the surface, coating of the surface with a crosslinked biocompatible polymer, chemical modification with biocompatible functional groups, or immobilization of a compatibilizing agent such as heparin or other biocompatible substances. Thus, any fibrous material having sufficient strength to survive in the in vivo environment may be used to form a textile graft, provided the final textile is biocompatible.

The graft material 22 may include a bioremodelable material such as reconstituted or naturally-derived collagenous materials, extracellular matrix (ECM) material, submucosa, renal capsule membrane, dermal collagen, dura mater, pericardium, fascia lata, serosa, peritoneum or basement membrane layers, or intestinal submucosa, including small intestinal submucosa (SIS), stomach submucosa, urinary bladder submucosa, or uterine submucosa. One non-limiting example of a suitable remodelable material is SURGISIS® BIODESIGN™ from Cook Medical (Bloomington, Ind.). Another suitable remodelable material is the graft prosthesis material described in U.S. Pat. No. 6,206,931 to Cook et al., which is incorporated herein by reference in its entirety. Additionally, or alternatively, the graft material 22 may be made of any of the materials described in U.S. Pat. No. 7,407,509 to Greenberg et al. or U.S. Patent Application Pub. No. 2009/0171451 by Kuppurathanam et al., which are incorporated herein by reference in their entirety.

At least one support structure, shown as a series of stents 30, is coupled along the graft body 20 between the inflow and outflow ends 27, 28. The stents 30 may move to a radially expanded configuration where it has a larger cross-sectional area from a radially compressed configuration when unloaded from the delivery device. The stents 30 coupled to the graft body 20 may exert an outward force on an interior wall of the body vessel, providing support to the body vessel at the point of treatment and to maintain the main lumen 26 of the graft body 20 up to its full cross-sectional area. The support structure may be a single unitary structure or may comprise of a plurality of discrete stents, as shown.

In one example, the support stent structure may comprise of a plurality of discrete stents 30 longitudinally spaced from one another and coupled along the inner surface 23, the outer surface 24, or both of the graft body sidewall 25 via suture attachment ties 49. The stents 30 depicted are shown being defined by a plurality of interconnected unit stent members arranged in an undulating pattern, such as, for example, a zigzag or serpentine pattern. The term "stent" means any device or structure that provides or is configured to provide rigidity, expansion force, or support to a body part, for example, a diseased, damaged, or otherwise compromised body lumen. The stents 30 may include any suitable biocompatible material, including, but not limited to, fabrics, metals, plastics, and the like. Examples of suitable materials include metals such as stainless steel and nitinol, and plastics such as polyethylene terephthalate ("PET"), polytetrafluoroethylene ("PTFE") and polyurethane. The stents 30 may be "expandable," that is, it may be capable of being expanded to a larger-dimension configuration. The stents 30 may expand by virtue of its own resilience (i.e., self-expanding), upon the application of an external force (i.e., balloon-expandable), or by a combination of both. In one example, the stents 30 may have one or more self-expanding portions and one or more balloon-expandable portions. In one example, the stents 30 shown are self-expanding under their inherent resilience. An example of a suitable self-expanding stent includes Z-STENTS™, which are available from Cook Inc., Bloomington, Ind., USA. One or more stents may be made from a woven wire structure, a laser-cut cannula, individual interconnected rings, or another pattern or design.

In one example, a discrete first proximal stent 30a that is in close proximity to the inflow end 27 of the graft body 20 may be disposed along the inner surface 23 of the graft material 22 to define an outer proximal annular bare region 42. The outer proximal annular bare region 42 along the outer surface 24 of the graft body 20 extends between the inflow end 27 of the graft body 20 and the axial length of the inwardly disposed first proximal stent 30a so that the exterior graft does not include a support stent structure. A discrete second proximal stent 30b may be positioned proximate and distal to the first proximal stent 30a. The second proximal stent 30b may be disposed on the inner surface 23 (as shown) or along the outer surface 24. The first and second proximal stents 30a, 30b may have a series of respective peaks 32a, 32b formed by proximal bends and a series of respective valleys 34a, 34b formed by distal bends. The relative position of the first and second proximal stents 30a, 30b may be arranged in a peak-to-peak arrangement where the valleys 34a are in alignment with the peaks 32b. Alternatively, the relative position of the first and second proximal stents 30a, 30b may be arranged in a peak-to-valley arrangement where the valleys 34a are in alignment with the valleys 32a. In one example, a discrete distal stent 30c that is in close proximity to the outflow end 28 of the graft body 20 may be also disposed along the inner surface 23 of the graft material 22 to define an annular distal bare region 51. The outer annular proximal bare region 42 and/or the annular distal bare region 51 along the outer surface 24 of the graft body 20 may not include a support stent structure, but may include barb or anchoring structures 47 to anchor the prosthesis to the body vessel and inhibit migration of the prosthesis. In other words, each of the annular bare regions 42, 51 may provide the prosthesis 10 an unobstructed sealing zone to be placed apposed to the walls of the body vessel.

The first proximal stent 30a and the second proximal stent 30b may be spaced longitudinally from one another by a distance (for example, between a valley 34a and a peak 32b) of between about 2 mm and about 20 mm, typically between about 5 mm and about 13 mm. In one example, the spacing between the first proximal stent 30a and the second proximal stent 30b may vary circumferentially around the graft body 20. The spacing between other portions of the support stent structure (for example, between other adjacent stents 30) may be similar to the spacing between the first proximal stent 30a and the second proximal stent 30b. In other examples, adjacent stents may be spaced any suitable distance from one another. The spacing between the adjacent stents may be sufficiently large to enable such flexibility of the graft body. In other words, an unsupported longitudinal section of the graft material of the graft body 20 between the adjacent stents may be sufficiently flexible to enable movement of the graft body. The stent sizing, spacing, and design may be determined so that there is no stent-to-stent contact even in tortuous anatomy. Stents preferably may be placed to maximize prosthesis flexibility while maintaining patency, as well as reducing material wear and stent fatigue.

With additional reference to FIGS. 2-5, the graft body 20 includes a trough portion 50 formed in the graft body 20 leading to a side branch 60. The trough portion 50 and the side branch 60 may be positioned generally within the main lumen 26 of the graft body. The trough portion 50 may be defined by a trough wall (shown as trough walls 52, 53, 54) extending between the outer surface 24 and the side branch 60. The trough portion 50 and the side branch 60 together define a transport conduit for devices or body fluid. The trough portion 50 may be further defined by a boundary 55 formed at the sidewall 25 along the outer surface 24 of the graft body 20. The boundary 55 includes a proximal side 55a and a distal side 55b, where the proximal side 55a is in closer proximity to the inflow end 27 than the distal side 55b. The side branch 60 may comprise of one or more of the graft materials described above. The side branch 60 includes an inner surface 63 and an outer surface 64. The side branch 60 may be configured as a generally tubular member having a substantially cylindrical shape. The inner surface 63 of the graft material 62 may define a branch lumen 66 extending longitudinally within the side branch 60 between a first end 67 and a second end 68 thereof. In one example, the trough portion 50 is coextensive with the branch lumen 66 to define the conduit. The trough portion 50 and the branch lumen 66 of the side branch 60 may be in fluid communication with each other and with the main lumen 26 of the graft body 20. The side branch 60 is shown as an internal side branch, although an external side branch is contemplated and may be configured in a similar fashion as that of the internal branch with the trough portion extending radially outward. Further, the orientation of the side branch may be in the antegrade or retrograde configuration or other positions, as further described.

The trough walls 52, 53, 54 and the side branch 60 may comprise of one or more of the graft materials described above. In particular, one, two, or all three of the trough walls 52, 53, 54 may be formed integrally with the graft body 20 and/or the side branch 60. Each of the of trough walls 52, 53, 54 includes respective first ends 52*a*, 53*a*, 54*a* disposed approximate the radial position of the sidewall 25 of the graft body 20 and respective second end 52*b*, 53*b*, 54*b* disposed closer to the longitudinal axis LA than the corresponding first ends.

Figure 4:
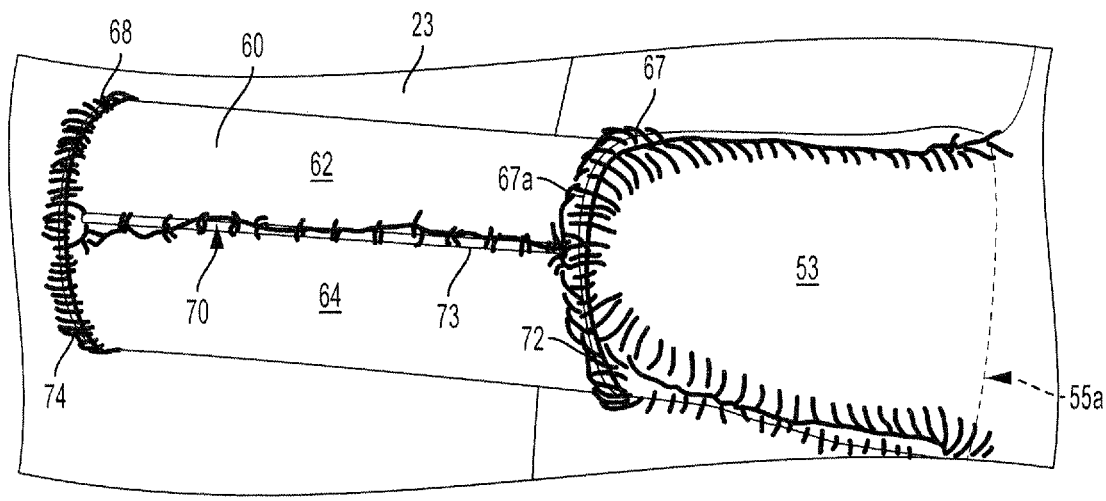
FIG. 4 depicts a magnified view of the side branch of the prosthesis depicted in FIG. 1.
Figure 5:
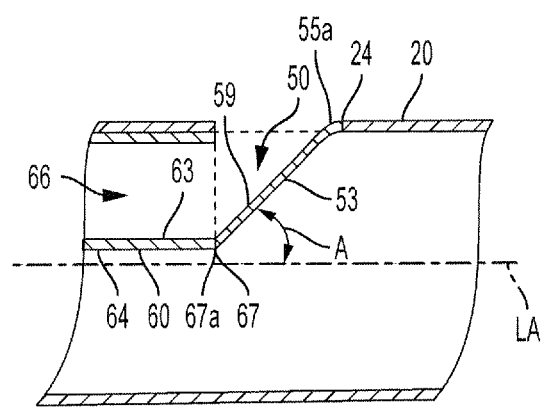
FIG. 5 is a cross-section partial view of the side branch of the prosthesis depicted in FIG. 1.

The intermediate trough wall 53 is disposed circumferentially in between the outer trough walls 52, 54 and extended between the sidewall 25 of the graft body 20 and the first end 67 of the side branch 60. The first end 53*a* of the intermediate trough wall 53 is defined extending circumferentially between the first end 52*a* of the outer trough wall 52 and the first end 54*a* of the outer trough wall 54 and defines the proximal side 55*a* of the boundary 55 of the trough portion 50. A fold line (shown in dashed lines) may be defined along the first end 53*a*. The intermediate trough wall 53 may extend from the sidewall 25 of the graft body 20 such that the second end 53*b* is coupled to a radial inner portion 67*a* of the first end 67 of the side branch 60, as shown in FIGS. 4-5. The intermediate trough wall 53 also may include outer edges 56*a*, 56*b*, as shown, extending between the first end 53*a* and the second end 53*b*. The outer edges 56*a*, 56*b* may taper inwardly toward the second end 53*b*.

In FIG. 5, the intermediate trough wall 53 may be oriented obliquely relative to the longitudinal axis LA at an angle A in the range of 30 degrees to 60 degrees to facilitate the guidance of devices passing through the side branch 60 and trough portion 50 to outside the prosthesis 10. The inclined intermediate trough wall 53 may face in the distal direction when the side branch 60 is biased in the retrograde configuration shown in the figures where the second end 68 is in closest proximity to the outflow end 28. Alternatively, the inclined intermediate trough wall 53 may face in the proximal direction when the side branch 60 is biased in the antegrade configuration where the second end 68 is in closest proximity to the inflow end 27.

The trough portion 50 may also be configured as providing an unobstructed surface without any suture stitching, reinforcing rings or frames, or other impediments. In one example, the intermediate trough wall 53 may be configured as a coextensive tab as described below extending into the main lumen 26 from the sidewall 25 of the graft body 20. To this end, a branch lumen facing surface 59 of the intermediate trough wall 53 is a continuous surface with the outer surface 24 of the sidewall 25 of the graft body 20. Accordingly, as a device passes through the side branch 60, the tip of the device slidably contacts the branch lumen facing surface 59 of the intermediate trough wall 53. The path along the branch lumen facing surface 59 allows the device the capability of sliding radially and longitudinally outward (or inward) along the surface path past the proximal side 55*a* of the trough portion 50 to outside (or inside) the prosthesis without snagging or otherwise impeding the advancement of such device. Also, one of the proximal side 55*a* or the distal side 55*b* may be unobstructed from stitching, for example, stitchless, or unobstructed from frames, for example, frameless, depending the direction of the branch 60. To this end, the stitching 61 may be discontinuous and/or a trough frame 58 may be partially enclosed along the boundary 55 to leave the branch lumen facing surface and one of the proximal or distal sides 55*a*, 55*b* of the boundary 55 is free and unobstructed to provide a smooth transition unobstructed surface between the trough portion 50 and the sidewall 25.

Figure 3:
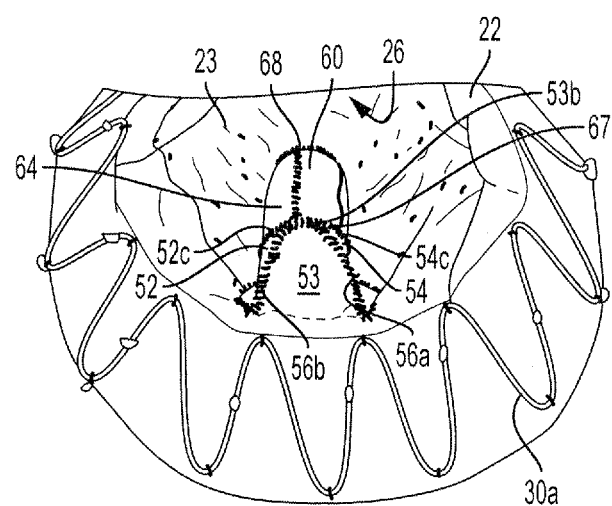
FIG. 3 is a perspective partial end view of the prosthesis depicted in FIG. 1, illustrating the side branch.

The outer trough walls 52, 54 are disposed along the intermediate trough wall 53 and extended between the sidewall 25 of the graft body 20 and the first end 67 of the side branch 60. The respective first ends 52*a*, 54*a* may be coupled to the graft body sidewall 25 by suture stitching. The second ends 52*b*, 54*b* may be coupled to the outer edges 56*a*, 56*b* and to a portion of the first end 67 of the side branch 60 by suture stitching. The outer trough walls 52, 54 may also include circumferential sides 52*c*, 54*c* that may extend between the respective first ends 52*a*, 54*a* and second ends 52*b*, 54*b* to the first end 67 of the side branch 60, as shown in FIG. 3.

When the side branch 60 is extending in the distal direction, as shown, the first ends 52*a*, 54*a* may be arranged to define the distal side 55*b* of the boundary 55 of the trough portion 50. In one example, the first ends 52*a*, 54*a* may be coupled to one another or may be integrally formed. The distal side 55*b* is shown as being arcuate or U-shaped, generally having a rounded bottom or a tapered bottom. Alternatively, the distal side 55*b* may have a circular, triangular, rectangular, or any other polygonal or non-polygonal geometric shape. When the side branch 60 is extending in the proximal direction, its proximal side would have the distal side 55*b* configuration, and vice versa with its distal side.

A trough frame 58 may be included along the distal side 55*b* of the trough portion 50 for further support. The frame 58 may add structural support to the trough portion 50 at the side branch opening and/or the attachment between the trough walls 52, 52, 54 and the graft material 22 of the graft body 20. The frame 58 may be configured as a rigid, semi-rigid, or flexible frame. Preferably, the frame 58 may be a flexible frame formed from any material known in the art including, for example, the materials described above with reference to the support stent structure or stent 30.

In FIG. 4, the side branch 60 may include at least one branch support structure 70 to aid at least in maintaining the branch lumen open and/or in biasing the side branch in a specific configuration. The side branch support structure 70 may include a single, unitary structure or a plurality of independent structures. The side branch support structure 70 and/or various portions thereof may be disposed on the inner surface 63 and/or the outer surface 64 of the side branch 60. Multiple branch support structures 70 may be positioned at any points along a length of the side branch 60. In one example, the side branch support structure 70 may be configured as a helical stent extending generally longitudinally and circumferentially along the side branch 60. The side branch support structure 70 also may be configured as one or more annular rings positioned along the length of the side branch 60. Alternatively, or additionally, any other type of stent including, for example, those described above in reference to the support stent structure or stent 30 may be used. The side branch support structure 70 may be formed from any material known in the art including, for example, the materials described above with reference to the support stent structure or stent 30.

In one example, the side branch support structure 70 may include one or more of the following: a ring support disposed about one of or both of the first end 67 and the second end 68 of the side branch 60, an axial strut disposed between the first and second ends 67, 68 of the side branch 60, and another axial strut disposed between the first and second ends 67, 68 disposed on the opposite side of the side branch 60. In one example, the side branch support structure 70 is defined by a first ring 72 coupled about the first end 67 of the side branch 60 with an axial strut 73 extending longitudinally away from the first ring 72 toward the second end 68 with suture stitching, and a second ring 74 coupled about the second end 68 of the side branch 60 with an axial strut (not shown) extending longitudinally away from the second ring 74 toward the first end 67 with suture stitching.

The trough portion 50 may be located along any portion of the graft body 20. In one example, the trough portion 50 may extend between adjacent struts of a stent (for example, the second proximal stent 30b). This may aid in positioning the side branch 60 near the inflow end 27 of the graft body 20 as further described below. Additionally, or alternatively, placement of the trough portion 50 between adjacent struts (for example, longitudinally at least partially between a valley of the second proximal stent 30b) may aid in supporting the trough portion 50 and the side branch 60. Additionally, or alternatively, the trough portion 50 may be attached to, or may encroach into, a region 40 of the graft body 20 defined between the spacing of two adjacent stents (for example, the first and second proximal stents 30a, 30b). The region 40 may be an unstented area between the adjacent stents. In one example, the location of the trough portion 50 does not encroach into the annular proximal and/or distal bare regions 42, 51 in order to keep these areas free of obstructions which may aid in sealing.

Figure 6:
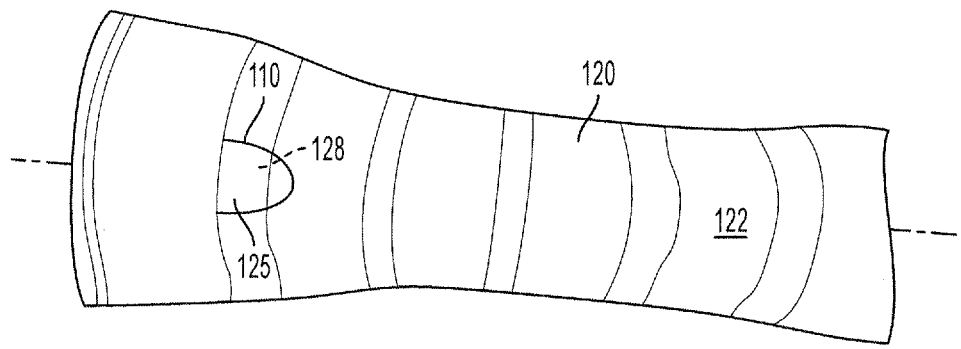
FIGS. 6-7 depict components used in one example of making a trough portion and a side branch with a graft material.
Figure 7:
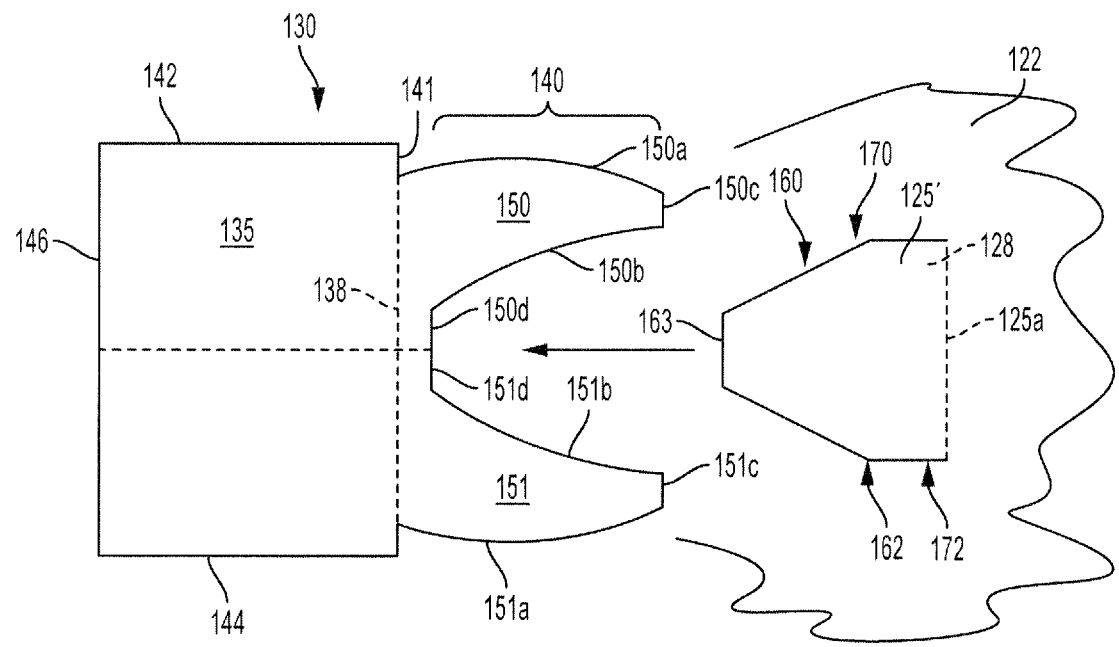

FIGS. 6-7 depict one example for manufacturing the trough portion 50 and the side internal branch (as shown) or the side external branch. The graft material 122, as described above, may be formed into a tube either may attachment of axial edges or woven or otherwise formed directly into a tube to define the tubular graft body 120. The graft body 120 may be prepared further by defining the locations of the stents, and ultimately the location of the trough portion and the side branch. A slit 110 may have a length shown extending circumferentially along the graft body 120. In other examples, the length of the slit 110 may extend longitudinally along the graft body 120, or in any other direction relative to the graft body. The slit 110 may have an arcuate shape or a U-shape or any other suitable shape, such as partially enclosed three, four, five, or more sided shapes with respect to the surface of the graft body 20 such that a tab portion 125 remains coextensive and integral with the sidewall of the graft body 120 and a perimeter of an aperture 128 is defined by slit 110. The cutout tab portion 125 is now movable within the aperture 128 relative to the surrounding graft material. The configuration of the slit 110 shown coincides with a branch extending in the distal direction, and a slit for a branch intended in the proximal direction would be a mirror image of the slit 110.

FIG. 7 depicts another piece 130 of the above described graft material that is configured to couple to the tab portion 125. Graft material piece 130 may include a branch forming portion 135 and an outer wall forming portion 140 (shown separated by a feature defining line 138 shown in a dashed line). The branch forming portion 135 may have a rectangular configuration. The outer wall forming portion 140 may have two discrete leg portions 150, 151 extending from an edge 141 of the branch forming portion 135, that correspond to the outer trough walls. The edge 141 may be coextensive with the feature defining line 138. The leg portions 150, 151 may be integrally formed from the same graft material as the branch forming portion 135. Alternatively, the leg portions 150A, 150B may be coupled to the edge 141 of the branch forming portion 135 by an attachment, such as but not limited to, suture stitching. The graft material piece 130 may be rolled in a manner to couple edges 142, 144 of the branch forming portion 135 together by an attachment, such as but not limited to suture stitching, to form a tubular structure that defines the side branch. When coupled, the edge 146 defines the second end of the side branch and the edge 141 and feature defining line 138 together define the first end of the side branch.

The leg portions 150, 151 may be mirror images of one another. For example, the leg portion 150 may be defined by edges 150a, 150b that are coupled to one another at a tip 150c. Edge 150a is shown extending to the edge 141, and edge 150b is shown extending short of the feature defining line 138 to define a foot region 150d. Likewise, the leg portion 150 has similarly situated edges 151a, 151b, tip 151c, and foot 151d. The edges 150a, 151a are associated with the first ends 52a, 54a of the outer trough walls 52, 54, respectively. The edges 150b, 151b are associated with the second ends 52b, 54b of the outer trough walls 52, 54, respectively. The edges 150b, 151b together define a slot shaped and sized to receive the tab portion 125.

To form a side branch, the graft body 120 may be inverted such that the inner surface is now on the outside, with the opposite occurring for the side external branch. The tab portion in FIG. 7 (now referred to as tab portion 125') includes a five-sided configuration. A pair of the sides of the tab portion 125' may form an edge 160, and a pair of the sides of the tab portion 125' may form an edge 162, opposite to the edge 160. The edges 160, 162 are coupled to one another by a tab tip 163. The edges 160, 162 are associated with the outer edges 56a, 56b of the intermediate trough 53. The tab tip 163 is associated with the second end 53b of the intermediate trough 53. The edges 160, 150b and the edges 162, 151b may be coupled together by an attachment, such as but not limited to, suture stitching. The edge 150a and the edge 151a may be coupled to the graft material perimeter sides 170, 172, respectively, that define the aperture 128 by an attachment, such as but not limited to, suture stitching, with the stitching having a hiatus at a base 125a of the tab portion 125. The tab tip 163 may be coupled to the foot 150d and the foot 151d, and the tips 150c, 151c may be coupled to the outer surface of the graft material and proximate the base of the tab portion 125 by an attachment, such as but not limited to, suture stitching. The foot 150d, 151d together may be associated with the radial inner portion 67a of the first end 67 of the side branch 60.

Figure 8:
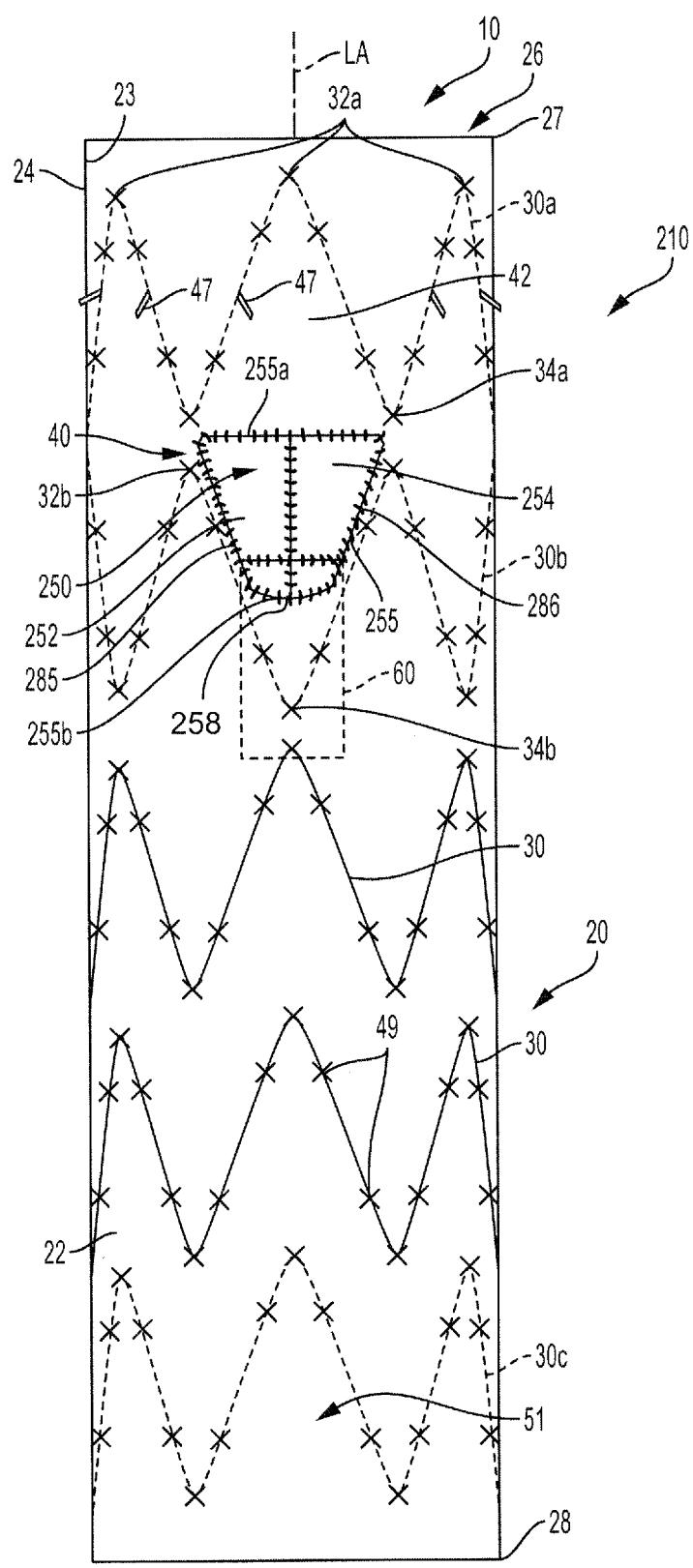
FIG. 8 is a side view of a prosthesis having another example of a trough portion in communication with a side branch.

FIG. 8 depicts another example of a trough portion 250 formed in the prosthesis (now referred to as prosthesis 210). The prosthesis 210 will have one or more of the features of prosthesis 10, and the following description will use the same reference numerals as used in the description of the prosthesis 10, except where there are differences.

The trough portion 250 may be formed in the graft body 20 of the prosthesis 210 leading to the side branch 60. The trough portion 250 is defined by trough walls 252, 254 extending between the outer surface 24 of the graft body 20 and the side branch 60. The trough portion 250 and the side branch 60 together define a transport conduit for devices. The trough portion 250 may be further defined by a boundary 255 formed at the sidewall 25 along the outer surface 24 of the graft body 20 as having a proximal side 255a and a distal side 255b. The trough walls 252, 254 and the side branch 60 may comprise of one or more of the graft materials described above. Each of the of trough walls 252, 254 includes respective first ends 252a, 254a disposed approximate the radial position of the outer surface 24 of the graft body 20 and respective second end 252b, 254b disposed closer to the longitudinal axis LA than the corresponding first ends. Further, the each of the of trough walls 252, 254 includes respective circumferential first sides 252c, 254c and circumferential second sides 252d, 254d, disposed opposite to corresponding sides 252c, 254c, each coupling the respective first and second ends together.

The first ends 252a, 254a may be arranged to define the proximal side 255a of the trough portion 250, which may be extend circumferentially in a linear fashion. To this end, the proximal side 255a is disposed circumferentially in between the first sides 252c, 254c. The first ends 252a, 254a and the second ends 252b, 254b are defined extending circumferentially between the respective first sides 252c, 254c and corresponding second sides 252d, 254d. The trough walls 252, 254 together may be oriented obliquely relative to the longitudinal axis LA at an angle in the range of 30 degrees to 60 degrees to facilitate the guidance of devices passing through the side branch 60 and trough portion 250 to outside the prosthesis 210. The trough walls 252, 254, when inclined, may face in the distal or proximal directions depending on whether the side branch 60 is biased in the retrograde or antegrade configuration.

The respective first ends 252a, 254a may be coupled to the graft body sidewall 25 by suture stitching. The respective first sides 252c, 254c may also be coupled to the graft body sidewall 25 by suture stitching. The second ends 252b, 254b may be coupled to the first end 67 of the side branch 60 by suture stitching. The respective second sides 252d, 254d may also be coupled together by suture stitching.

The coupling of the second sides 252d, 254d may form a single seam along a portion of the trough portion 250. The single seam is shown in the middle of the trough portion; however, it can be appreciated that the trough walls 252, 254 may be different shapes in order to position the seam away from the middle to aid in the removal of potential obstructions along the middle of the path. Alternatively, it can be appreciated that a third trough wall (not shown) may be inserted between the trough walls 252, 254 and coupled along the second sides 252d, 254d to form two seams. The relative position of the two seams may be pushed farther away from the middle by the size of the third trough in order to aid in the removal of potential obstructions along the middle of the path. Alternatively, it can be appreciated that the trough walls 252, 254 may be integrally formed into a single unit having no seam to aid in the removal of potential obstructions along the middle of the path.

The second ends 252b, 254b and sides 252c, 254c may be arranged to define the distal side 255b of the trough portion 250. The distal side 255b is shown as being as a half-diamond shape, generally having a tapered bottom end. Alternatively, the distal side 255b may have a circular, triangular, rectangular, or any other polygonal or non-polygonal geometric shape. A trough frame 258 may be included along the distal side 255b and/or the proximal side 255a of the trough portion 250 for further support. The frame 258 may add structural support to the trough portion 250 at the side branch opening and/or the attachment between the trough walls 252, 254 and the graft material 22 of the graft body 20. The frame 258 may be a flexible frame formed from any material known in the art including, for example, the materials described above with reference to the support stent structure or stent 30.

The trough portion 250 may be located along any portion of the graft body 20. In one example, the trough portion 250 may extend between adjacent interconnected struts of a stent (for example, the second proximal stent 30b). This may aid in positioning the side branch 60 near the inflow end 27 of the graft body 20. Additionally, or alternatively, placement of the trough portion 250 between adjacent struts (for example, longitudinally at least partially between a valley of the second proximal stent 30b) may aid in supporting the trough portion 250 and the side branch 60. Additionally, or alternatively, the trough portion 250 may be attached to, or may encroach into, the unstented region 40 of the graft body 20 defined between the spacing of two adjacent stents (for example, the first and second proximal stents 30a, 30b). In one example, the location of the trough portion 250, particularly the proximal side 255a) does not encroach into the annular proximal and/or distal bare regions 42, 51 in order to keep these areas free of obstructions which may aid in sealing.

Figure 9:
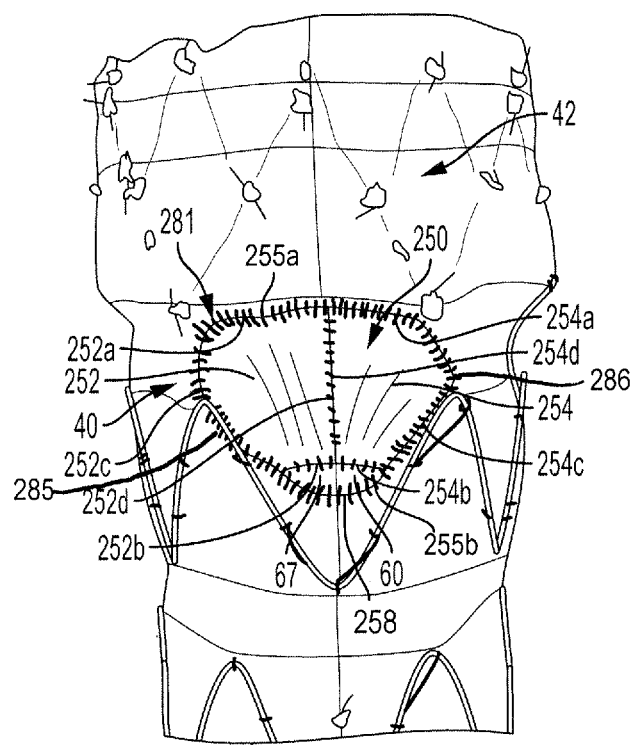
FIG. 9 is a perspective partial view of the trough portion and the side branch of the prosthesis depicted in FIG. 8.
Figure 10:
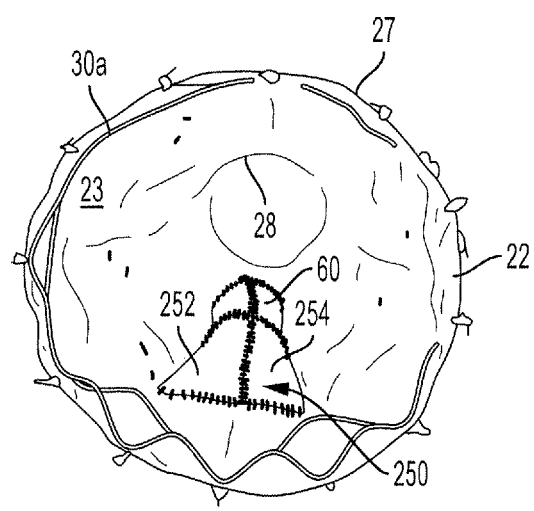
FIG. 10 is a perspective partial end view of the prosthesis depicted in FIG. 8, illustrating the side branch.

The trough portion 250 and the side branch 60 in the prosthesis 210 may be formed from pieces of graft material. At least a portion of the piece of graft material may be rolled into a generally tubular shape to form the side branch 60. A section of graft material may be removed from a zone of the prosthesis to define an aperture 281 positioned between first and second proximal stents of the prosthesis. The size and shape of the perimeter of the aperture 281 correspond to the size and shape of the boundary 255 of the trough portion 250. The aperture 281 and thus the boundary 255 may be a half-diamond shape as shown in FIGS. 8-9. For example, the boundary 255 may include a pair of opposite circumferential sides 285, 286 tapering inward along the same direction of the side branch lumen along the corresponding nearest struts of a stent (shown as the second proximal stent 30b). The circumferential sides 285, 286 couple the proximal side 255a and the distal side 255b. The distal side 255b may be curved or disposed linearly. The proximal side 255a may be aligned with a plane extending along the inflow end 27 perpendicular to the longitudinal axis LA. The intersection of the ends of the proximal side 255a and the ends of the circumferential sides 285, 286 may be chamfered. The distal side 255b may be longitudinally positioned along an intermediate area (40% to 60% of the length) of the corresponding nearest struts of a stent. To this end, the circumferential length of the distal side 255b may be at least 40% of the circumferential length proximal side 255a.

Pieces of the graft material are sized and shaped to define the trough walls 252, 254. The second sides of the trough walls may be coupled together. The second ends of the trough walls may be coupled to the first end 67 of the side branch 60 and a distal portion of the perimeter that defines the aperture 281 proximate the first end of the side branch. The first ends and the first sides of the trough walls may then be coupled along the remaining portions of the perimeter.

In one example, the trough walls 252, 254 and the side branch 60 are formed integrally from a single piece of graft material into a single tubular structure. Here, one of the end openings of the single tubular structure is associated with the second end of the branch lumen and is axially facing along the longitudinal axis. The opposite end of the end openings of the single tubular structure is associated with the trough portion and is radially facing away from the longitudinal axis. The opposite end opening is then coupled to the perimeter of the aperture 281.

In any of the examples described herein, the trough portion or walls may be coupled by an attachment to the graft body and/or the support stent structure or stent of the prosthesis by any suitable method. The coupling attachment between the graft materials and stent structure by suture stitching, wire, staples, clips, bonding agents, or other methods that may be used to achieve a secure attachment.

Preferably, the coupling between the components forms a fluid-tight seal, including using a sealant or adhesive, along or in combination with another coupling mechanism such as stitching, to enhance the seal. For example, the trough portion may be stitched to the graft material of the graft body and further stitched to one or more struts of the first proximal stent using a running blanket stitch. Alternatively, the trough portion may be formed during weaving of the graft material of the graft body. The trough portions described herein may be coupled to the graft body and/or the support stent structure or stent.

The side branch and trough portion configuration can be modified to accommodate first and second proximal stents having any configuration. The trough portion may be configured to align generally with the struts of the first and/or second proximal stents. The trough portion and/or the side branch portion may be positioned generally within the lumen of the prosthesis. The side branch portion may be attached to (or integral with) and extend from the trough portion. For the side branch to fit appropriately, the trough design may be customized to fit the side branch diameter and/or length. The graft material of the trough walls and/or the side branch may be formed from the same or a different material than the material used to form the graft material 22.

It is further contemplated that the prosthesis 10 or 210 may have multiple branches. For example, the prosthesis may have two, three, or more branches attached to the graft body. The various branches may be positioned at different longitudinal and circumferential positions along the graft body. In this manner, the side branches may be configured to align with, for example, the left subclavian, left common carotid, and/or inanimate arteries. Additionally, or alternatively, the prosthesis may be configured for placement at various other positions within the vasculature of the patient.

One or more radiopaque markers may be included to provide radiographic visualization of the position of the prosthesis 10 or 210 when placed in a body vessel of a patient. A plurality of radiopaque markers, which according to one example may be provided in the form of gold beads, may be coupled to the graft body (for example, the graft material and/or the support structure or stent), the trough portion (for example, the graft material of the trough walls and/or the perimeter of the aperture), and/or the side branch (for example, the graft material and/or the support structure) to facilitate imaging of various desired locations along the length of the prosthesis. The radiopaque markers may be positioned at the inflow end and/or the outflow end of the graft body. The radiopaque markers also may be positioned proximate the trough portion and/or the side branch to facilitate proper alignment with a branch vessel.

The trough portions 50, 250 and the side branches 60 described herein may have other modifications. Additionally, or alternatively, the trough portion may enable movement of the side branch relative to the graft body. For example, the trough portion may be configured to enable the graft material of the trough walls to move (for example, inward or outward with respect to the longitudinal axis of the graft body). Attachment of the side branch to the surface of the graft body may aid in securing the position and configuration of the side branch. Although the side branch may be biased toward a particular direction, as described above, the side branch may be movable in any direction relative to the graft body. The opening of the second end of the side branch may be directed in any direction (for example, proximal, distal, or transverse) relative to the longitudinal axis of the graft body. For example, the side branch may be configured to pivot about the trough portion between the retrograde configuration and the antegrade configuration. In other examples, the side branch may be substantially unbiased. In other words, the graft material of the trough walls may be sufficiently flexible that the graft material does not exert a biasing force on the side branch.

In any of the examples described herein, movement of the side branch 60 relative to the graft body may aid in aligning the side branch with a branch vessel such as, for example, the left subclavian artery to account for any misalignment between the opening in the graft body material and the side branch vessel. If the prosthesis is placed such that the side branch is slightly proximal of the ostium of the branch vessel, the side branch may be moved into the antegrade configuration to extend generally in the direction of the branch vessel. If the prosthesis is placed such that the side branch is slightly distal of the ostium of the branch vessel, the side branch may be moved into the retrograde configuration to extend generally in the direction of the branch vessel. In this manner, movement of the side branch may compensate for misalignment between the side branch and the branch vessel upon deployment of the prosthesis.

Such movement of the side branch 60 may aid in delivering the prosthesis 10 or 210 by several different methods including femoral delivery, brachial delivery, axillary delivery, subclavian delivery, and/or transapical delivery. For example, the prosthesis may be delivered via the femoral artery with the side branch in the retrograde position. In the retrograde position, the opening of the second end of the side branch may face proximally so that a catheter extending through the side branch also may extend proximally. This may aid in cannulating a branch vessel and/or snaring the catheter from the branch vessel when delivering the prosthesis from distal to the branch vessel. In other words, the side branch may be oriented in the retrograde configuration to receive a catheter, as further described below, extending generally proximally for delivery of the prosthesis using a retrograde approach (for example, a femoral approach).

In another example, the prosthesis 10 or 210 may be delivered using brachial, axillary, or transapical delivery with the side branch 60 in the antegrade position. In the antegrade position, the opening of the second end of the side branch may face distally so that a catheter extending through the side branch also may extend distally. This may aid in cannulating a branch vessel and/or snaring the catheter from the branch vessel when delivering the prosthesis from proximal to the branch vessel. In other words, the side branch may be oriented in the antegrade configuration to receive a catheter, as further described below, extending generally distally for delivery of the prosthesis using an antegrade approach (for example, a brachial, axillary, or transapical approach). The ability to move the side branch relative to the graft body may aid in delivering the prosthesis from distal or proximal to a target branch vessel (for example, using a retrograde or an antegrade approach). The opening of the second end of the side branch, and thus the catheter extending through the side branch, may be directed proximally or distally to face the branch vessel regardless of whether the prosthesis is delivered from distal or proximal to the branch vessel. Thus, the same prosthesis may be used regardless of the delivery approach selected by the physician.

A common practice in treating patients with Type B dissection with conventional endografts is to use a through wire starting from the subclavian artery, snaring the wire, and pulling the wire out the femoral artery. In this way, the subclavian approach is used to facilitate cannulation of the true lumen, yet allow delivery of the device from the femoral approach. A transapical approach would also have similar benefits. Specific delivery system modifications (for example, the location of the cannula, the location of catheters, the orientation of the device, the length of the tip, etc.) may exist for each delivery paradigm.

The prosthesis 10 or 210 may be sized and shaped for placement within the vasculature of a patient as further described below. The preferred size and shape of the prosthesis depends on the anatomy in which it is to be implanted. Physiological variables, deployment characteristics, and other factors also may contribute to the determination of a proper size and shape of the prosthesis. For example, the prosthesis may have a size and shape suitable for placement in the aortic arch, and/or the descending aorta. To that end, the prosthesis may be configured for placement within the thoracic aorta with the inflow end being placed in the aortic arch and the outflow end being placed in the descending aorta. The sidewall opening of the side branch may be configured to align with the ostium of a branch vessel, such as the left subclavian artery. In one example, the prostheses 10, 210 described herein may be configured as a single branch thoracic endograft that provides flow to the left subclavian artery or the left common carotid artery as described. Alternatively, multiple branches may be provided. In other examples, the prostheses may be applied to extend coverage more proximal by using the single branch for the left common carotid artery and relying on flow through the vertebrals or an extra-atomic bypass to maintain flow to the left subclavian artery. The prostheses may be applicable to treat aneurysms and/or dissections that require more proximal coverage than a standard thoracic stent graft might allow.

The graft body 20 of the prosthesis 10 or 210 may have a diameter, for example, ranging from about 10 mm to about 50 mm, typically from about 22 mm to about 46 mm. The diameter of the graft body 20 may be constant along the length thereof. Alternatively, the graft body may be tapered such that the diameter of the graft body may vary along the length thereof. For example, the diameter of the graft body may taper from a larger diameter to a smaller diameter in a proximal to distal direction. In one example, the graft body may have a proximal to distal taper of up to about 10 mm. A tapered graft body may be advantageous for placement within a narrowed aorta. Such a narrowed aorta may be common when treating aortic dissection. The side branch 60 may have a diameter, for example, ranging from about 6 mm to about 24 mm, typically from about 8 mm to about 12 mm. The diameter of the side branch may be constant along the length thereof. Alternatively, the side branch may be tapered such that the diameter of the side branch may vary along the length thereof. The prosthesis 10 or 210 may be deployed in combination with various other prostheses to effectively bridge an aneurysmal and/or dissected portion of the vasculature. In one example, the length of the side branch may be between about 8 mm and about 25 mm. In one example, the diameter and the length of the side branch may be about 8 mm diameter (for example, the side branch may be configured as an 8 mm reinforced tube)×18 mm length. In other examples, the side branch may have any suitable diameter and/or length.

Further, the trough portion for the prosthesis 10 or 210 may be positioned near the inflow end 27 of the graft body 20. For example, the trough portion may be placed between about 5 mm and about 30 mm, between about 10 mm and about 25 mm, or between about 15 mm and about 20 mm from the inflow end of the graft body. Additionally, or alternatively, the graft body may have a longitudinal length, for example, ranging from about 10 cm to about 200 cm.

Additionally, or alternatively, the side branch may be spaced from the inflow end of the graft body by between about 0.25% and about 30%, between about 0.5% and about 25%, or between about 0.75% and about 20% of the length of the graft body. The proximity of the side branch to the inflow end of the graft body may aid in aligning the side branch with a branch vessel (for example, the subclavian artery) while landing the proximal end of the graft body between two adjacent branch vessels (for example, the subclavian artery and the carotid artery) without occluding the branch vessels as shown in FIG. 11.

Figure 11:
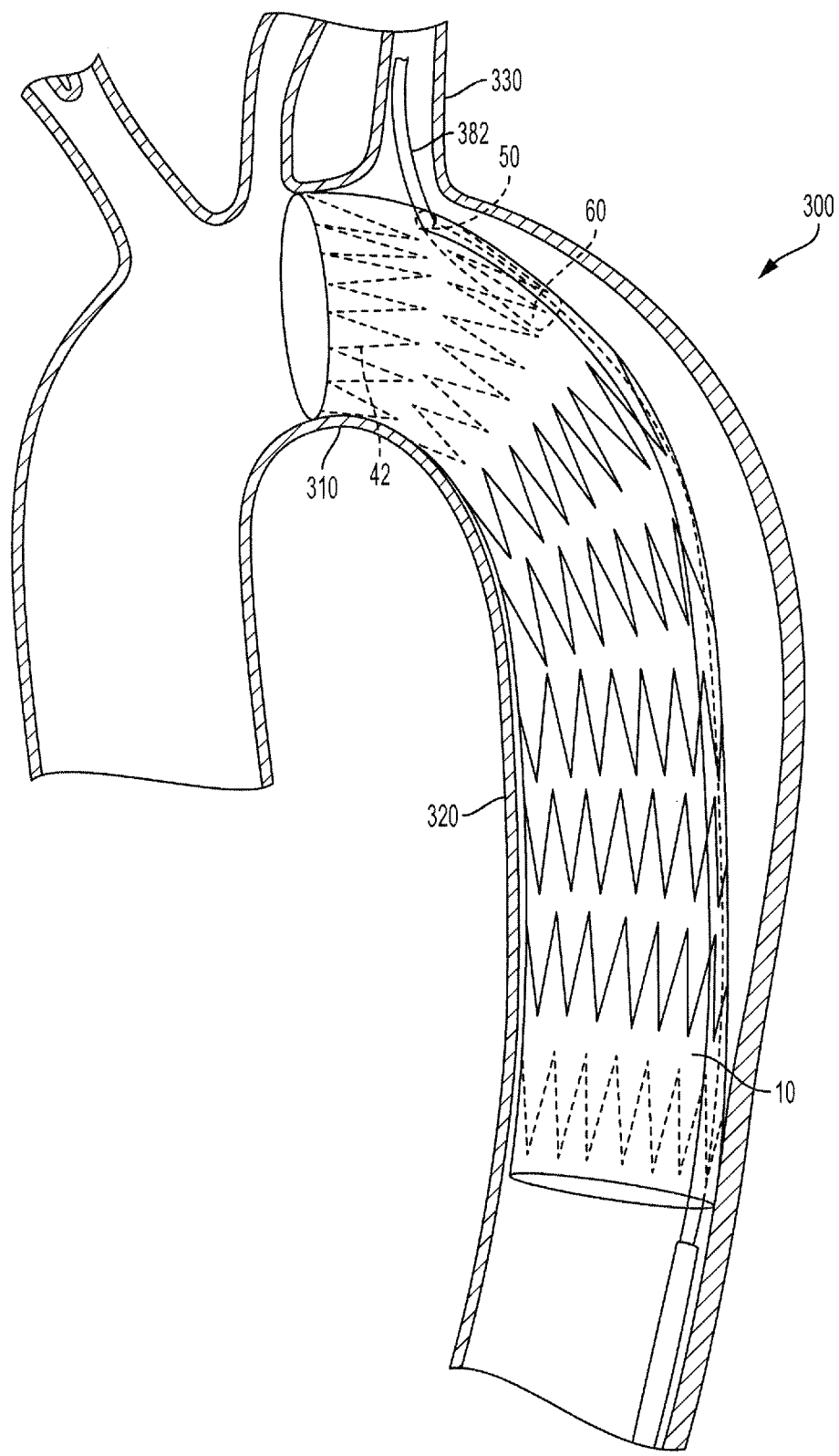
FIG. 11 depicts a catheter passing through a trough portion and a side branch of a prosthesis into a branch vessel, where the prosthesis is implanted into a primary body vessel.
Figure 12:
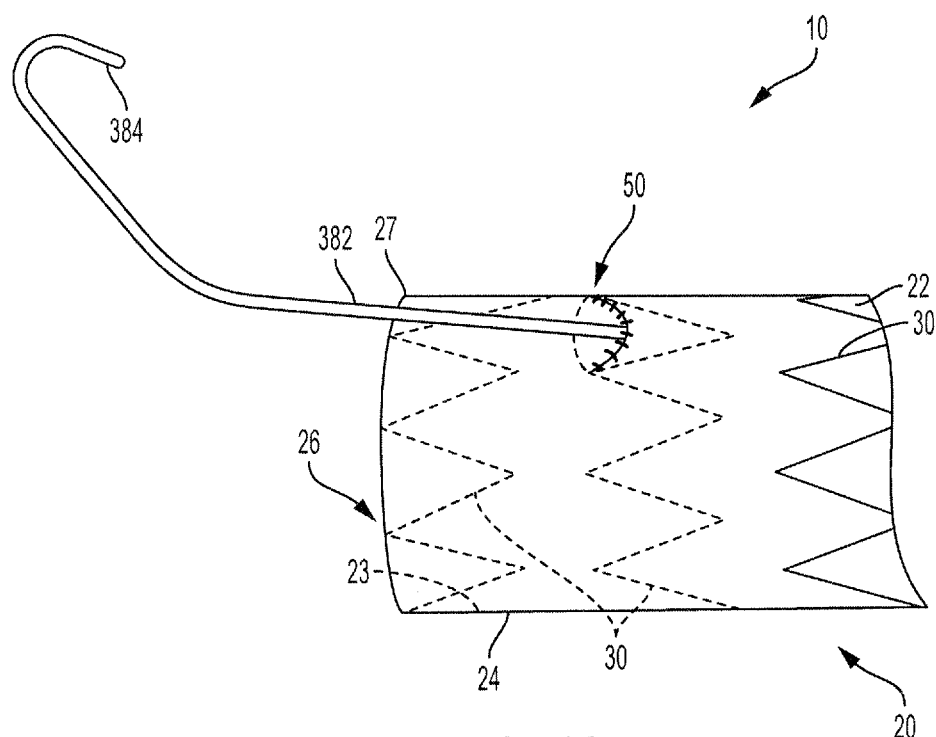
FIG. 12 depicts a catheter passing through a trough portion and a side branch of a prosthesis.
Figure 13:
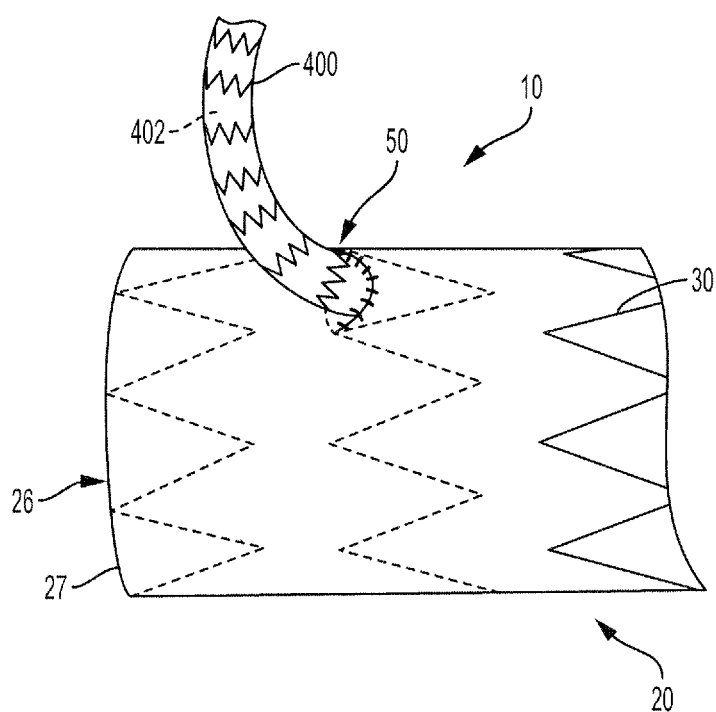
FIG. 13 depicts a connection prosthesis extending out from a trough portion and a side branch of a prosthesis.

As shown in FIGS. 11-13, catheters or other devices may be inserted though the side branch and out the trough portion of the prosthesis 10 or 210 to access a part of the anatomy. Such devices may be inserted through the vessels after the expansion of the prosthesis or may be preloaded as described. As shown, a catheter 382, which may be configured to facilitate cannulation of a branch vessel, movement of the side branch 60, and/or insertion of a branch prosthesis within the side branch 60. The catheter 382 may be preloaded in the prosthesis 10 prior to introduction of the prosthesis within a patient. When preloaded as part of a delivery system, a proximal region 384 of the catheter 382 may be advanced through the main lumen 26 of the graft body 20 from the outflow end 28 toward the inflow end 27. The proximal region 384 of the catheter 382 then may be advanced through the side branch 60 to exit the prosthesis 10 as shown in FIG. 12. This configuration of the preloaded catheter 382 (i.e., extending proximally within the prosthesis 10 from the outflow end 28) may be desirable for retrograde delivery of the prosthesis (for example, femoral delivery). In other examples, the catheter 382 may be advanced through the main lumen 26 from the inflow end 27 toward the outflow end 28. This configuration of the preloaded catheter 382 (i.e., extending distally within the prosthesis 10 from the inflow end 27) may be desirable for antegrade delivery of the prosthesis (for example, brachial, axillary, or transapical delivery). The catheter 382 may sit in a separate groove in a tip of a delivery device. It can be appreciated that pulling back a sheath may expose the catheter 382 to allow a physician to snare and withdraw the preloaded catheter through a sheath in the subclavian artery. In other examples, the catheter 382 may include a catch member such as a hook, loop, or eye at the proximal region 384 to aid the physician in snaring the catheter 382. Additionally, or alternatively, a guidewire (now shown) may be received within a lumen of the catheter 382. The guidewire may be preloaded in the prosthesis as described above with respect to the catheter 382 and/or received within the preloaded catheter. The guidewire may facilitate the placement of various other devices, devices, or components (for example, the balloon described below) within the vasculature of the patient.

The prosthesis 10 or 210 may be compressed into a delivery configuration and mounted onto a deployment device such as an introducer. Any type of deployment device suitable for deploying a branched stent graft may be used. For example, suitable deployment devices may include those described in U.S. Pat. Nos. 7,488,344 and 7,537,606 to Hartley et al.; U.S. Pat. No. 7,611,529 to Greenberg et al.; and U.S. Patent App. Pub. No. 2009/0204198 by Jensen et al.; which are incorporated by reference herein in their entirety. Although the following description will generally refer to femoral delivery of the prosthesis, the prosthesis also may be delivered via subclavian delivery, brachial delivery, transapical delivery, axillary delivery, or any other desirable form of delivery. A person having ordinary skill in the art will appreciate that the configuration and/or orientation of the prosthesis, the delivery device, the catheter, and/or any components thereof may be modified depending on the chosen delivery method. Such modifications are within the scope of this disclosure.

The prosthesis 10 or 210 may be radially compressed into the delivery configuration on a delivery catheter and covered by an outer sheath. To deploy the prosthesis, the operator may slide or retract the outer sheath over the delivery catheter, thereby exposing the prosthesis. The prosthesis may expand outwardly upon removal of the sheath. The operator may directly manipulate the introducer, which may provide the operator with a relatively high degree of control during the procedure. Further, such deployment devices may be compact and may have a relatively uniform, low-diameter radial profile, allowing for atraumatic access and delivery.

With reference to FIG. 11, using such a suitable delivery system, a physician may introduce the prosthesis 10 or 210 in the delivery configuration into the femoral artery and guide the prosthesis into position within the aortic arch 310 and/or the descending aorta 320. The prosthesis 10 or 210 may be positioned using the radiopaque markers such that the side branch 60 is generally aligned in the vicinity of the ostium of the left subclavian artery 330. The sheath of the delivery system, which may constrain the prosthesis in the delivery, radially compressed configuration, may be retracted distally to allow the prosthesis to expand from the delivery configuration.

The prosthesis 10 or 210 may remain at least partially restrained in a radially compressed configuration, for example, by one or more diameter reducing ties. Diameter reducing ties may be applied to the support structure or stent 30 of the graft body 20. The diameter reducing ties may be applied to the proximal and distal stents of the graft body 20 to retain the inflow and outflow ends 27, 28 in a reduced diameter configuration after retraction of the sheath, such as by tied thread and trigger wire arrangement. The struts may be released upon removal of the trigger wire to allow expansion of the stent. The diameter reducing ties also may be configured as any other type of constraining member capable of reducing the diameter of a stent of the prosthesis.

Retraction of the outer sheath also may expose the catheter 382, when preloaded, extending from the side branch 60 and trough portion of the prosthesis 10 or 210 as shown in FIG. 11. Otherwise, the catheter 382 may be advance to the position after prosthesis expansion. The catheter 382 may be snared and pulled though a sheath positioned within the left subclavian artery 330. A balloon may be tracked over the catheter 382 and positioned within the side branch 60. The balloon may be manipulated to adjust the orientation of the side branch 60 relative to the graft body of the prosthesis. In one example, a first end of the balloon may be positioned and movable within the main lumen of the graft body of the prosthesis to move the side branch, if desired. For example, a catheter associated with the balloon may be manipulated (for example, advanced, retracted, rotated, or bent) to adjust the orientation of the balloon, and thus the orientation of the side branch 60, with respect to the graft body. The orientation of the side branch 60 may be adjusted to align the side branch with the left subclavian artery 330.

The trough portion 50 of the prosthesis 10 may be beneficial for providing a tracking path for passing devices such as the catheter 382 therethrough. The continuous smooth surface (that is, without stitching) of the intermediate trough wall and/or the omission of stitching, frame or other obstruction from the boundary of the trough may provide a smooth transition surface between the trough portion and the sidewall. The operator physician may pass devices, such as wires, catheters and sheaths, through the side branches easier and more efficiently to speed of the operation time. The size and shape of the trough portion of the prosthesis 10, 210 so as to not encroach the annular proximal bare region 42 may provide the prosthesis 10 or 210 the use of the full unobstructed sealing zone when placed apposed to the walls of the body vessel and avoid possible leak paths contributed by stent or frame structures in this region.

It can be appreciated that a branch prosthesis 400, such as a stent graft, may be deployed within the side branch 60 and out the trough portion of the prosthesis 10 or 210 as shown in FIG. 13. The branch prosthesis 400 may be delivered over the catheter 382 and deployed within the side branch 60 using any known method. The branch prosthesis 400 may extend longitudinally, for example, proximally from the side branch 60, relative to the graft body 20. The branch prosthesis 400 may extend between a position within the main lumen 26 of the graft body 20 and a position external to the graft body 20. A lumen 402 of the branch prosthesis 400 may be in communication with the main lumen 26 of the graft body 20. In one example, the branch prosthesis 400 may extend between the main lumen 26 of the graft body 20 and a branch vessel such as the left subclavian artery 330. In other words, a first end of the branch prosthesis may be deployed within the branch lumen of the side branch 60 of the prosthesis and a second end of the branch prosthesis 400 may be deployed within the left subclavian artery 330. In this manner, the branch prosthesis 400 may couple the prosthesis 10 or 210 to the left subclavian artery to create a continuous fluid passageway therebetween.

The delivery systems described herein may need various other components in order to obtain a delivery and deployment system that is optimally suited for its intended purpose. These include and are not limited to various outer sheaths, pushers, trigger wires, stoppers, guide wires, and the like. For example, the Zenith® Thoracic Aortic Aneurysm Endovascular Graft uses a delivery system that is commercially available from Cook Inc., Bloomington, Ind., and may be suitable for delivering and deploying an aortic prosthesis in accordance with the present embodiments.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

The invention claimed is:

1. A prosthesis, comprising:
   a tubular graft body including a sidewall extending between an inflow end and an outflow end and defining a main lumen between the outflow and inflow ends;
   a stent structure coupled along the graft body;
   a trough extending from the sidewall and comprising:
      a first trough wall composed from a portion of the sidewall of the tubular graft body,
      a first trough wall boundary bounding the first trough wall, the first trough wall including a first end, a second end longitudinally spaced from the first end, and first and second edges between the first and second ends, and
      first and second opposed outer trough walls attached to the first trough wall along the first and second edges of the first trough wall boundary and extending outwardly from the first trough wall, and
      a trough boundary;

and
   a tubular branch defining a branch lumen and extending from the trough towards one of the inflow or outflow ends of the graft body, wherein the trough, the branch lumen, and the main lumen are in fluid communication, and wherein the first trough wall presents a continuous surface to the branch lumen.

2. The prosthesis of claim 1, wherein the trough extends between adjacent struts of a stent of the stent structure.

3. The prosthesis of claim 2, wherein the first and second opposed outer trough walls taper inwardly.

4. The prosthesis of claim 1, wherein the stent structure comprises a series of stents each including a plurality of interconnected struts in an undulating pattern and at least a portion of the trough is disposed between a pair of interconnected struts.

5. The prosthesis of claim 1, wherein the side branch and the first and second opposed outer trough walls are integrally formed from a single graft material piece.

6. The prosthesis of claim 1, wherein the trough boundary includes a trough frame about at least a portion of a perimeter of the trough boundary.

7. The prosthesis of claim 6, wherein the first and second opposed outer trough walls includes the trough frame.

8. The prosthesis of claim 1, wherein the first trough wall comprises a tab cut into the sidewall having at least one edge that is unattached to the sidewall such that an opening is formed in the sidewall.

9. The prosthesis of claim 8, wherein the first and second opposed outer trough walls are attached to the at least one edge.

10. The prosthesis of claim 9, wherein the opening in the sidewall forms an open end of the branch lumen.

11. The prosthesis of claim 10, wherein the opening is perpendicular to a longitudinal axis of the tubular graft body.

12. The prosthesis of claim 11, wherein the opening opens to one of the inflow or outflow ends.

13. The prosthesis of claim 1, wherein the first trough wall is oriented obliquely relative to a longitudinal axis of the tubular graft body.

14. A prosthesis, comprising:
   a tubular graft body defining a main lumen extending between an inflow end and an outflow end of the graft body;
   a stent structure coupled along the graft body;
   a trough defined by a boundary formed at a sidewall of the graft body and extending away from the side wall, wherein a portion of the boundary provides an unobstructed transition surface between the trough and the sidewall; and
   an internal branch defining a branch lumen and extending away from the trough towards one of the inflow or outflow ends of the graft body within the main lumen, wherein the trough, the branch lumen, and the main lumen are in fluid communication, and wherein the trough includes a branch lumen facing surface that is a continuous surface with an outer surface of the sidewall of the graft body and an inner surface of the branch lumen.

15. The prosthesis of claim 14, wherein the stent structure comprises a plurality of stents, a first proximal stent of the plurality of stents being disposed approximate the inflow end of the graft body along an inner surface of the graft body, a second proximal stent being disposed distal to the first proximal stent by a spacing, wherein the second proximal stent includes a pair of interconnected struts, and at least a portion of the boundary is disposed between the pair of interconnected struts.

* * * * *